United States Patent [19]
Yang

[11] Patent Number: 6,160,617
[45] Date of Patent: *Dec. 12, 2000

[54] HIGH RESOLUTION IMAGING MICROSCOPE (HIRIM) AND USES THEREOF

[75] Inventor: Mary M. Yang, San Jose, Calif.

[73] Assignee: Kairos Scientific, Inc., Santa Clara, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/229,462

[22] Filed: Jan. 12, 1999

Related U.S. Application Data

[63] Continuation of application No. 08/562,272, Nov. 22, 1995, Pat. No. 5,859,700.

[51] Int. Cl.[7] .................................................... G01J 3/00
[52] U.S. Cl. ......................... 356/300; 356/317; 356/417
[58] Field of Search .................................. 356/300, 319, 356/326, 328, 317, 318, 417; 382/128, 129, 133, 134

[56] References Cited

PUBLICATIONS

Ackleson, S.G. et al., "Ocean Optics: The Seasonal Time Scale II," EOS 71:108 (1990).

Aiken, J. et al., "The SeaWiFS CZCS–Type Pigment Algorithm," NASA Technical Memorandum 104566, 29:1–37 (1995).

Boyer, M. et al., "Senescence And Spectral Reflectance In Leaves Of Northern Pin Oak (Quercus Palustris Muenchh.)," Remote Sensing of Environment 25(1):71–87 (1988).

Curran, Paul J. et al., "Reflectance Spectroscopy Of Fresh Whole Leaves For The Estimation Of Chemical Concentration," Remote Sensing Of Environment 39(2):153–166 (1992).

Curran, Paul J. et al., "Remote Sensing of Foliar Chemistry," Remote Sensing Of Environment 30(3):271–278 (1989).

Curran, Paul J. et al., "The Effect Of A Red Leaf Pigment On The Relationship Between Red Edge And Chlorophyll Concentration," Remote Sensing Of Environment 35(1):69–76 (1992).

Danson, F.M. et al., "Red–Edge Response To Forest Leaf Area Index," International Journal Of Remote Sensing 16(1):193–188 (1995).

Holligan, P.M. et al., "Satellite And Ship Studies Of Coccolithophore Production Along A Continental Shelf Edge," Nature International Weekly Journal of Science 304:339–342 (1983).

Millie, D.F. et al., "High–Resolution Airborne Remote Sensing Of Bloom–Forming Phytoplankton," Journal of Phycology 28:281–290 (1992).

Weaver, E.C. et al., "Factors Affecting The Identification Of Phytoplankton Groups By Means Of Remote Sensing," NASA Technical Memorandum 108799, pp. 1–121 (1994).

Yang, M.M., "Applications Of Imaging Spectroscopy In Molecular Biology: I. Screening Phynthetic Bacteria," Biotechnology 6:939–942 (1988).

Yang, M. M., "Digital Imaging Spectroscopy of Microbial Colonies," American Biotechnology Laboratory May 18–20, 1994.

Yang, M.M., "Raman Spectroscopic Investigations of Hydrothermal Solutions", Doctoral Thesis (abstract), Princeton University (1987).

Youvan, D.C., "Imaging Sequence Space," Nature International Weekly Journal of Science, 369:79–80 (1994).

Primary Examiner—F. L. Evans
Attorney, Agent, or Firm—McCutchen, Doyle, Brown & Enersen, LLP

[57] ABSTRACT

The invention pertains to a high resolution imaging microscope, and more specifically, to a digital imaging spectrophotometer (DIS) configured to enable the direct determination of the ground state absorption spectra of microscopic samples from violet to near infrared. The instrument is capable of simultaneously recording hundreds of spectra, and can, using image processing techniques identify features (such as a single microbial cell) on a microscope slide or thin section. The invention additionally relates to the use of such an instrument.

35 Claims, 7 Drawing Sheets

Relative spectral irradiance curves for quartz-tungsten-halogent (QTH), mercury, and xenon lamps. QTH has a logarithmic, monotonic drop-off in intensity in the blue, whereas multiple narrow band emissions are found in mercury and xenon lamps.

Typical single cell spectra of:
A) *Rhodomonas salina*
B) *Porphyridium cruentum*
C) *Chroosmonas mesostigmatica*
D) *Tribonema aequale*
E) *Prorocentrum lima*
F) *Amphora sp.*
G) *Dunaliella tertiolecta*
H) *Tetraselmis sp.*

HIGH RESOLUTION IMAGING MICROSCOPE (HIRIM) AND USES THEREOF

This is a continuation of U.S. application Ser. No. 08/562,272, filed Nov. 22, 1995 now U.S. Pat. No. 5,859,700.

FIELD OF THE INVENTION

The invention pertains to a high resolution imaging microscope, and more specifically, to a digital imaging spectrophotometer (DIS) configured to enable the direct determination of the ground state absorption spectra of microscopic samples from violet to near infrared. The instrument is capable of simultaneously recording hundreds of spectra, and can, using image processing techniques identify features (such as a single microbial cell) on a microscope slide or thin section. The invention additionally relates to the use of such an instrument.

BACKGROUND OF THE INVENTION

Imaging spectroscopy is defined as the combined analysis of both spatial and spectral information so that each picture element (pixel) in a two dimensional scene includes a third dimension of spectral information. This means that the spectrum of any pixel or group of pixels within an image can be measured. Digital Imaging Spectrophotometers/Spectroscopy (DIS) combine imaging spectroscopy with digital image processing techniques. DIS is a powerful screening tool which can be considered functionally equivalent to tens of thousands of spectrophotometers operating in parallel. DIS was developed for the rapid and noninvasive analysis of bacterial mutants directly on petri dishes.

The ColonyImager, is a low cost, user-friendly, high performance digital imaging spectrophotometer which has been redesigned and brought to market by KAIROS Scientific (Santa Clara, Calif.). This instrument supports spectral acquisition in both transmission and reflectance mode. In addition, fluorescence emission images can be acquired by selection of an appropriate long-pass filter. In order to obtain radiometrically calibrated spectra, one must correct for the wavelength response of the detector and optics. This has been successfully accomplished so that the quality of spectra is as good or better than that obtained from a double beam spectrophotometer. With 5 nm bandpass and data taken at 5 nm intervals, the ColonyImager can easily detect 2.5 nm spectral shifts. This is close to the limit imposed by a diffraction grating; therefore, conventional spectrophotometers are not much better in spectral resolution.

The first workstation based imaging spectrophotometer for analysis of petri plates was sold in 1991 and the PC based ColonyImager was brought to market in 1993, which also marked the first international sale of this device. This instrument has recently been featured in two technical articles and three scientific reviews, including a product review in *Nature* and a chapter in *Methods in Enzymology*. KAIROS is the sole source for this state-of-the-art equipment.

SUMMARY OF THE INVENTION

Figure 1:
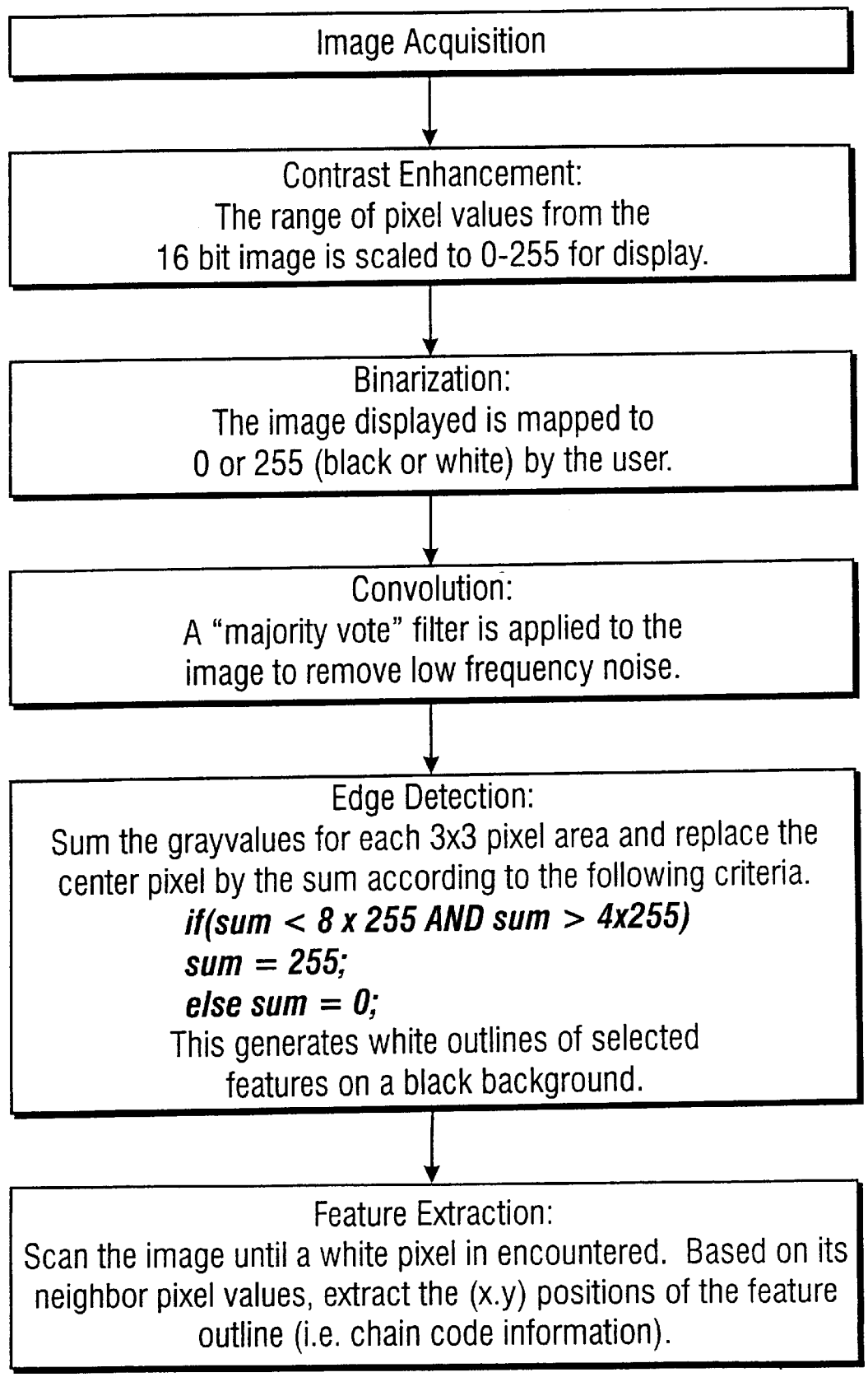
FIG. 1 shows the general process for extracting features of a captured image

The invention pertains to a high resolution imaging microscope, and more specifically, to a digital imaging spectrophotometer (DIS) configured to enable the direct determination of the ground state absorption spectra of microscopic samples from violet to near infrared. The instrument is capable of simultaneously recording hundreds of spectra, and can, using image processing techniques identify features (such as a single microbial cell) on a microscope slide or thin section. The invention additionally relates to the use of such an instrument.

In detail, the invention provides a high resolution imaging microscope, wherein the microscope comprises a digital imaging spectrophotometer that enables the direct determination of the ground state absorption spectra of microscopic samples from approximately 400 nm to approximately 950 nm at 2 nm resolution with approximately 1 micron refraction limited spatial resolution.

The invention also provides a method for simultaneously obtaining spectral information from a plurality of microscopic objects which comprises:

A. employing a high resolution imaging microscope, wherein said microscope comprises a digital imaging spectrophotometer that enables the direct determination of the ground state absorption spectra of microscopic samples from approximately 400 nm to approximately 950 nm at 2 nm resolution with approximately 1 micron refraction limited spatial resolution, to view said plurality of objects; and B. permitting said spectrophotometer to obtain said spectral information from said objects.

The invention also provides the ability to simultaneously display and process spectral information from all features or a subset of selected features in the microscope's field of view. The invention combines massive spectral data processing and display with image processing and also allows the real-time correlation of spatial and spectral information.

The invention also provides the ability to sort stored spectral information and display this information in the form of a contour plot.

DESCRIPTION OF THE PREFERRED EMBODIMENTS

A digital imaging spectrophotometer (DIS), previously configured for macroscopic samples, has been redesigned and constructed. The prototype instrument, a High Resolution Imaging Microscope (HIRIM) enables the direct determination of the ground state absorption spectra of microscopic samples from the violet (400 nm) to the near infrared (950 nm) at 2 nm resolution with refraction limited (approximately 1 micron) spatial resolution. Hundreds of spectra can be recorded simultaneously, using image processing techniques to identify features (e.g. single microbial cells) on a microscope slide or thin section. This massive amount of data can be analyzed, sorted and collectively displayed in a pseudocolored manner concurrent with the spatial information.

HIRIM is a microscopic embodiment of DIS with different hardware components from the macroscopic instrument. The software associated with HIRIM takes advantage of previously developed software and includes many additional features not included with the ColonyImager. The implementation of DIS microscopy should not be confused with single spectroscopic readings of selected spots by certain commercial microscopes (e.g. Nikon). DIS microscopy will record the spectrum of every pixel or feature in the scene, simultaneously.

HIRIM has been used to simultaneously acquire spatial and spectral information of hundreds of algae and cyanobacteria immobilized on slides. Peaks due to chlorophyll, phycobilins, carotenoids and other pigments can be readily determined from individual cell spectra and internal cell structures.

With HIRIM, particularly in concert with the modified software interface CyberDIS (KAIROS Scientific, Inc., Santa Clara, Calif.), users are provided with a tool that enables one to point to a pixel or group of pixels in an image (i.e., field of view of a microscope) and recall the associated spectrum. This means that individual spectra of specific features such as single cells or internal cell ultrastructure may be determined.

The CyberDIS software includes over 50,000 lines of C code written for Microsoft Windows 3.1 (Youvan, D. C. 1994. *Nature* 369: 79–80; Yang, M. M. 1994. *American Biotechnology Laboratory* May: 18–20). Although many instrument control and image processing tools are available in the current version of CyberDIS, a number of major software changes and additions are made for the microscopic version. These modifications include: 1) adaptation of instrument control and image display functions for a large format camera, 2) image magnification, 3) pixel integration of odd shaped features from chain-code information, 4) ability for the user to draw on the screen to outline regions of interest, and 5) automated feature extraction. The general process for extracting features of the captured image is shown in FIG. 1.

One of the first goals in the software development of HIRIM was to facilitate the hardware testing and incorporation of the new detector. The most efficient way to accomplish this was to modify the CyberDIS software to interface with multiple cameras. An initial task involves creating wrapper functions for camera control, image display, and image processing. These functions will make the differences between the two cameras (in terms of communications protocol, image sizes, and many other factors) transparent to the rest of the program. For code maintenance and commercial purposes, this will provide the same "look and feel" and ease of use regardless of which detector is attached.

Another software development goal addresses the problem of image storage and finite disk storage size. Due to storage and speed considerations, HIRIM software currently calculates spectra during the course of a scan and saves only a few selected images at specified wavelengths (e.g., 450 nm, blue; 550 nm, green; 650 nm, red). These stored images can then be individually image processed or combined at a later time. For example, CyberDIS can reconstruct a 'true color' image from the three narrow band stored images specified above. To better utilize PC disk space (currently in the 1 gigabyte capacity), various image compression algorithms and image formats, such as tiff and gif, may be employed.

The contour plots within CyberDIS enable rapid screening and comparison of large numbers of spectra. The sorting algorithms that have been implemented can be used to segregate spectral categories or to enable detection of unusual spectra or spectral shifts in a small proportion of the features. Spectral sorting routines can be performed according to several different criteria having to do with the position and intensity of various absorption bands. One method uses a sum-of-the-square-of-the-differences error function which scales as $$\prod_{i=1}^{N}(N-i) \qquad \text{Eq. 1}$$

where N is the total number of spectra and i is a counter. In fact, an exhaustive sort would involve searching N! possible combinations. Eq. 1 can be shown to scale better than $N^2$ which is still computationally feasible. As the number different spectra increases, the ability of the spectral sorting algorithms to differentiate individual spectra becomes more critical. The efficiency of the sorting algorithm can be evaluated from the results of mixing all 25 strains together into one microscopic field.

Eq. 2 indicates that spatial resolution can be increased by interposing a medium with a high refractive index.

$$d = \frac{\lambda}{2n\sin\mu} = \frac{1}{\text{resolving power}} \qquad \text{Eq. 2}$$

This value is set by the index of refraction of air (n=1) and the index of refraction of the lens glass (n=1.515). With a good lens, matched cover glass thickness, and using an oiled contact between the condenser and the slide, it is possible to obtain an overall numerical aperture of 1.5. Using this value, the minimum limit of resolution for a light microscope using violet light is 0.13 microns. When magnification exceeds the limit of resolution, each object point in the image becomes a small object called an Airy disc, and the resulting image becomes not only blurred and lacking in detail, but may even show unreal structures.

The contributions of this phenomenon and its affect on the spectra can be analyzed using single cells or small features in the 1–2 micron size range. Correlations and confirmations of physiological features within the cell can easily be made with published morphological information obtained from other techniques such as electron microscopy. In addition to the objective and projection lens of the microscope, HIRIM magnification is also a function of the CCD chip and pixel sizes. Using different combinations of objectives, projection lenses, and condensers, the optimal (optical train) configuration for the analyses of very small features can be determined.

The index of refraction for any medium is defined as the ratio of the velocity of light in a vacuum to its velocity in that of the medium. Snell's law relates the velocities (V) and index of refraction (n) of different mediums with the angle of incidence (sin(i)) and the angle of refraction (sin(r)) for a given wavelength.

$$V/V_2 = \sin(i)/\sin(r) = n_2/n_1 \qquad \text{Eq. 3}$$

Spherical cells may act as a crude lens by either dispersing or concentrating light. If the cell has a higher index of refraction than the embedding medium, it will act as a converging lens and concentrate light within the cell image. This may have an effect on the spectra of organisms with calcium carbonate or silica shells. For such cases, different embedding mediums may be employed, and the spectra calculations may be restricted to those pixels which are well within cell walls and away from areas where sudden changes in index of refraction occur. These feature selection guidelines also apply to membranes, plastids, and the nuclei within a cell's infrastructure.

For purposes of developing HIRIM optics and hardware, a permanent (fixed, sectioned, and stained) slide obtained from the quality control department of Sigma Chemicals (St. Louis, Mo.) is preferably employed as a 'test target', in addition to the slides previously described containing live photosynthetic organisms. This will enable the same sample to be returned to the slide for successive measurements of the same feature, thus enabling optical refinements to be compared without variation in the target. Hard to control parameters such as cell to cell spectral variation, cell morphology, and cell motility can then be eliminated.

During some HIRIM runs, images acquired at the beginning of a scan are in focus whereas images acquired towards the end of the run are not. This may reflect the severe physical demand placed on the microscope to maintain a constant vertical distance of a few microns over a period of approximately one hour as images were serially transferred from the K6. Since the K7 will decrease the scan time by a factor of twenty five (for comparable binned images), it should be easier to maintain constant focus throughout the scan. An alternative would be to decrease the numerical aperture since a lower NA provides a larger depth of field and so the focus drift would not be as critical. However, there is a tradeoff, because light collection is not as efficient with lower NA.

CCD insensitivity to blue light has limited some of the HIRIM measurements to wavelengths longer than 430 nm. One means for achieving this goal involves the use of coatings on the K7 chip which convert (through fluorescence mechanisms) blue light to green light, thereby providing the chip with greater sensitivity. Light sources which have greater intensity in the blue (e.g., Xe) may also be employed.

Current sorting algorithms either include or exclude data from wavelength intervals with equal weighting. More sophisticated algorithms might weight particular wavelengths heavier than others and include the possibility of specifying groups of wavelengths that are not in one contiguous interval. Success of such algorithms is easily evaluated by mixed populations: the more species that are correctly segregated into blocks of spectra in the contour plot, the better is the algorithm. If these algorithms are sufficiently robust, then performance on unknown samples should also be superior to the procedure summarized by Eq. 1. Other proposed additions to the spectral sorting algorithms include derivative analysis and the capability to process spectra from multiple datasets. Changes will be made to the software so that all functions in CyberDIS, excluding data acquisition, can be used to analyze other datasets which consist of spatially registered images taken at multiple wavelengths (e.g., AVIRIS "datacubes").

A typical HIRIM run involves focusing and aligning the objects in a selected field of view under brightfield illumination, such as QTH or alternative light sources such as Xenon or Mercury. The light source is then switched to the monochromator and an image acquired at a wavelength midrange for the planned scan. Many features of interest (typically, several hundred) can be selected from this image. One reference feature from a 'clear' region of the image is also selected. This reference feature is analogous to the 'blank' in a double beam, conventional spectrophotometer and its grayvalues are used as the $I_O$ in the Beer Lambert calculation. A calibration run is performed to correct for the system response. The raw data processed from HIRIM may be analogous to the datacubes or image stacks from remote sensing, wherein images are sequentially acquired at different wavelengths. Without further user interaction, the CyberDIS software directs the actual spectral scan, calculates spectra for all features, and then displays the results on the PC monitor within three interactive windows; the image window, the conventional plot window, and the contour plot window.

Each row in the contour plot corresponds to the spectrum of each of the features located in the image. The absorbance values are color coded according to the colorbar at the bottom of the contour window. Low absorbance is black, high absorbance is white, and intermediate absorbances are encoded as a logical continuum of colors. The CyberDIS user interface of HIRIM provides a convenient means to correlate features in the image with spectra. The computer's mouse can be used to point to any feature in the image or any row in the contour map with a real-time update of the spectrum in the lower left window. Moving the feature selection circle on the image causes the red bar in the contour plot to move to the correct row; conversely, moving the red bar causes the corresponding feature to be marked and its spectrum displayed in the plot window.

One of the unique features of the software interface for HIRIM is the ability to sort spectra and display them in the form of pseudocolored contour maps.

Uses of the HIRIM

Studies of Biogeochemical Cycles

Photosynthesis is the conversion of light to chemical energy and forms the basis of life on Planet Earth. This process is also a key contributor to global biogeochemical cycles for carbon, phosphate, and nitrogen. Through the conversion of $CO_2$ and water, photosynthesis generates 160 billion metric tons of carbohydrate per year (Campbell, N. A., "Biology", 2nd ed., Benjamin Cummings, Redwood City, Calif. (1990)). It is thought that 30–60% of global photosynthesis is attributable to phytoplankton (Upper Ocean Processes. *Report of the U.S. GOFS Working Group on Upper Ocean Processes*. 1988, Woods Hole Oceanographic Institution, Massachusetts). Recent studies indicate that marine phytoplankton are responsible for the transformation of $50 \times 10^{15}$ g of $CO_2$/year (Sullivan, C. W., Arrigo, K. R., McClain, C. R., Comisco, J. C., and Firestone, J., 1993. *Science* 262: 1832–1837). As these organisms die and sink to the ocean floor, they are ultimately buried in oceanic sediments or redissolved at greater depths due to increased pressure. On land, the carbon assimilated by plants is frequently returned to the atmosphere by deforestation, the burning of fossil fuels, and the decay of plant matter by microorganisms and fungi. The effects of deforestation are now a major concern, not only because of its contribution to harmful greenhouse gases, but also because of its effects on biodiversity.

Although the focus of the following discussion concerns marine organisms (phytoplankton and algae), the Digital Imaging Spectrophotometer (DIS) of the present invention can also be used to analyze intact land plants.

Airborne and Satellite Remote Sensing

Airborne and satellite remote sensing of ocean color can be used to make synoptic measurements of the abundance and distribution of the oceanic biomass. These instruments have profoundly changed the field of oceanography and the understanding of near surface biological processes. The Coastal Zone Color Scanner (CZCS) was the first spacecraft instrument devoted to the measurement of the world's oceans. This instrument viewed the ocean with one thermal IR band (10.5–12.5 micrometers) and five other spectral bands in the visible and near IR (443, 520, 550, 670 and 750 nm). The band at 750 nm is used to discriminate between land, clouds, and ocean while the four visible bands were chosen for pigment absorption. The total signal measured by airborne and satellite remote sensing is a combination of backscattered radiation from the intervening atmosphere, the sea-surface, and the upper water column. Chlorophyll concentrations can be determined after corrections for atmospheric and surface reflections, and contributions from suspended sediments and dissolved organics with the aid of in water or bio-optic algorithms (Dickey, T. D. 1991. *Rev. Geophys.* 29:383–413). Although the understanding of bio-optics has progressed significantly, it is far from having fully exploited the wealth of information that can be obtained from such methodologies. The executive summary and recommendations from a recent bio-optic workshop (Bio-Optics. *Report of the U.S. GOFS workshop on bio-optics*. Boulder Colo. 1993., Woods Hole Oceanographic Institution, Massachusetts) stress the need for detailed examination of the causes of bio-optical signals, new and improved calibration methods, instrumentation, and further development of bio-optic models. High priority is also given to the interpretation of new and existing measurements including accuracy, precision, and quantification of resolution.

A number of studies have shown that pigment composition may be used to identify specific groups of phytoplankton and algae (Rowan, K. S., "Photosynthetic Pigments of Algae". Cambridge University Press, New York (1989); Green, J. C., Leadbeater, B. S. and Diver, W. L. (eds) "The Chromophyte Algae. Problems and Perspectives". Oxford Science Publ. (1989)). Some of these identifications have already been made from remote sensing instruments Weaver, E. C. and Wrigley, R., 1994, Factors affecting the identification of phytoplankton groups by means of remote sensing. *NASA Tech. Mem.* 108799; Sakshaug, E., Johnsen, G., Samseth, O., and Volant, Z. 1991. In, *Environment Northern Seas*. p91–100; Hooker, S. B., Esias, W. E., Geldman, G. C., Gregg, W. W. and McClain, C. R., An Overview of SeaWiFS and Ocean Color, *NASA Tech. Mem.* 104566. Vol1 (1992); Millie, D. F., et al. 1992. *J. Phycol.* 28:281–290). However, because of cost, data transmission times and other factors, a continuous wavelength range is not sampled. The selection of wavelengths and bandwidths used for remote sensors (e.g., SeaWiFS, MERIS, HIRIS, AVIRIS) is very critical. It is desirable to make a systematic comparison of spectra to identify the wavelength sets which will be the most informative for remote studies. In terms of primary productivity, it is also helpful to determine specific wavelengths that distinguish between chlorophyll and its degradation products. The major pigment groups involved in photosynthesis will now be described.

Photosynthetic Pigments

Almost all photosynthetic organisms possess chlorophyll. Bacteriorhodopsin in halobacteria is an exception if light-driven proton pumping is considered to define photosynthesis rather than the fixation of $CO_2$. The chemical formulae and selected spectra of the major forms of this pigment are given in Fong, F. K. ed., "Light Reaction Path of Photosynthesis", Springer-Verlag. 1982, herein incorporated by reference. The absorption spectra of purple bacteria, cyanobacteria, green, red and brown algae are provided in Hader, D., and Tevini, M. "General Photobiology", Pergamon Press, (1987) herein incorporated by reference (as used herein, Chl=chlorophyll, BChl=bacteriochlorophyll, Car=carotenoids, P.C.=phycocyanin, P.E.=phycoerythrin, Fux=Fucoxanthin).

Green plants usually have both chlorophyll a and b. Chlorophyll c1 and c2 are found in brown algae and diatoms, whereas chlorophyll d is found in red algae. The bacteriochlorophylls a and b are found in some prokaryotic bacteria. In addition to their significance as ancestors of eukaryotic algae and higher plants, fundamental photosynthesis questions have also been answered from recent studies of bacterial prokaryotes. For example, the structural genes for the light reactions of photosynthesis have been discovered (Youvan, D. C. and Ismail, S. 1985. *Proc. Natl. Acad. Sci. USA* 82:63–67; Youvan, D. C., Bylina, E. J., Alberti, M., Begusch, H. and Hearst, J. E. 1984. *Cell* 37:949–957) and the crystal structure of the reaction center determined (Diesenhofer, J., Epp, O., Miki, K., Huber, R., and Michel, H. 1985. *Nature* 318:618–624) to atomic resolution. Furthermore, genetic engineering and spectral studies are being used to elucidate the primary pathways and time course of the conversion of light to chemical energy (Coleman, W. A. and Youvan, D. C. 1990. pp333–367. In *Annual Review of Biophysics and Biophysical Chemistry* 19:333–367).

Conjugated double bonds in the chlorophyll tetrapyrrole structure are responsible for absorption in the red and blue. Chlorophyll a has an absorption maximum at 430 nm and 663 nm when dissolved in methanol. These peaks are shifted in chlorophyll b to 453 and 642 nm due to the formyl group in ring B. Chlorophyll-protein complexes in photosynthetic organisms typically have absorption maxima shifted to longer wavelengths as compared to their solution spectra. The bandshape and position of peak maxima are also highly dependent on the protein environment. For example, bacteriochlorophyll a in the LHI complex absorbs at 878 nm which is a considerable red shift from the absorption in solution at 770 nm. Although all the bacteriochlorophyll a molecules bound to the LHII antenna are chemically equivalent, absorption occurs at two different wavelengths in the near IR (800 and 858 nm) because of differences in the binding sites. Similarly, the special pair bacteriochlorophylls and the two voyeur bacteriochlorophylls in the reaction center occur at 860 and 800 nm, respectively. The reaction center also binds two bacteriopheophytin molecules whose presence is noted by a peak at 760 nm. Pheophytins have similar chemical structures to the chlorophylls except that the central magnesium ion is replaced by two protons. Other photosynthetic pigments include the carotenoids and the phycobilins.

Carotenoids are yellow or orange long-chain tetraterpenes. The main carotenoids in green tissues are: β-carotene, lutein, violaxanthin, neoxanthin, antheraxanthin, and zeaxanthin. Most carotenoids found in algae have two cyclic end-groups linked by a $C_{18}$ chain (e.g., alloxanthin, fucoxanthin). The absorption spectra of carotenoids typically show three peaks in the blue region of the spectrum. Because of this higher energy absorption and large bandwidth, carotenoids extend the spectral range available for photosynthesis. In higher plants and green algae, these accessory pigments transfer their energy to the reaction center chlorophylls with 40–50% efficiency. In brown algae and diatoms, energy is transferred with essentially 100% efficiency. Carotenoids are also important in their ability to quench singlet state oxygen and thus protect the chlorophylls from triplet-mediated photooxidation. Care should be taken during pigment extraction since degradation products are easily formed due to oxidation, low or high pH, light, and heat or a combination of these factors (Rowan, K. S., "Photosynthetic Pigments of Algae," Cambridge University Press, New York (1989)).

Phycobilins are found in the light harvesting pigment protein complexes (i.e. phycobilisomes) of cyanobacteria and red algae. Absorption occurs over the range 470–650 nm, between the blue and red absorption peaks of chlorophyll a. Spectral properties are highly dependent on the type and number of phycobilins, steric relationships, and the protein environment. Each of these 600 nm diameter, rod shaped complexes contain multiple phycobiliprotein subunits and hundreds of phycobilins. The absorption and emission maxima shift to the red in going from phycoerythrin to phycocyanin to allophycocyanin. This order reflects the flow of energy in a phycobilisome to the chlorophylls in the photosystems. Since this energy transfer is very efficient (approximately 100%), phycobiliproteins in intact phycobilisomes are virtually non-fluorescent. However, when the reaction center trap is decoupled or removed, intense fluorescence with large Stokes shifts (87 nm for phycoerythrin) can be observed. In contrast, the emission maxima of chlorophyll a in solution is only shifted by 7 nm (Hader, D., and Tevini, M. "General Photobiology", Pergamon Press, (1987)).

The spectra of photosynthetic pigments are affected by many factors. In the analysis of airborne and satellite remote sensing, it is therefore desirable that ground-truthing and laboratory based studies are also performed. A major challenge is the fact that organisms are not uniformly distributed in the water column and so it is difficult to determine their contribution to the overall signal. As compared to the open ocean, coastal analyses are further complicated by the presence of suspended sediment and dissolved organics (i.e. gelbstoff). The relative proportions of various pigments are important, as is the identification of specific organisms present from their spectral signatures. Phytoplankton community structure information might be used to assess environmental effects such as ozone depletion, pollutants and nutrient availability. One of the most popular methods for pigment separation and quantification is HPLC. The accuracy of these calculations is limited by 1) incomplete pigment extraction, 2) pigment "package" effects, and 3) differences in the intracellular absorption properties of the pigments classified within each of the pigment groups.

It would be useful to complement the above measurements with spectra taken directly from the intact organism. Microscopic analyses can provide information on organisms which cannot be cultured or may otherwise have escaped detection. Recent studies have identified a new group of very abundant picoplankton (concentrations greater than $10^5$ per ml) which account for a significant proportion of global productivity (Chisholm, S. W., et al. 1988. *Nature* 334:340–343). Size distribution and surface properties of microorganisms are also important contributors to the overall signal. Bright areas in airborne (AVHRR) and satellite (CZCS) images have been correlated to the presence of coccolithoporids (Ackleson, G., 1990. *EOS* 71:108; Holligan, P., Voillier, M., Harbour, D. S., Camus, P., and Champagne). These organisms play an important role in the global carbon cycle since their skeletal composition is almost pure calcium carbonate. There is also evidence that coccolithoporids are a source of dimethyl sulfide; of which the oxidation product sulfur dioxide serves as cloud condensation nuclei. It is apparent that simultaneous microscopic determination of hundreds of individual organisms and their in situ spectra as proposed herein, would be very useful.

Analysis of Vegetation

The analysis of plants can also be facilitated by the present invention. However, in contrast to oceanic phytoplankton, pigment changes in land vegetation are perhaps more familiar and dramatic as seen in seasonal variations of foliage. The spectacular display of autumn color in temperate zones is due to the new synthesis or unmasking of colored pigments: anthocyanins, carotenoids, and xanthophylls which usually follow a decline in chlorophyll production. Although visually striking, this process is referred to as senescence and is an aging process which eventually leads to death. Likewise, many other color changes in plants are an indication of disease (e.g., phyloxera) or nutrient stress (e.g., drought). In addition to estimates of primary production, one of the goals of remote sensing studies of vegetation is the early detection of stress.

Remote spectral studies of foliage can be loosely broken down into three spectral ranges: 1) 400–800 nm visible absorption by photopigments, 2) 800–1400 nm near infrared transitions dominated by the internal geometry of the leaf, and 3) 1400–2500 nm IR region, where direct contributions from water absorption is important (Boyer et al., *Remote Sens, Env*. 25:71–87 (1988)). Reflectance spectroscopy of whole leaves in the visible to NIR have been used to estimate concentrations of chlorophyll, protein, starch, sugar, and water (Curran et al., *Remote Sens. Env*. 39:153–166 (1992)). The point of maximum slope which occurs between 680 and 740 nm is commonly referred to as the "red-edge". This feature has been widely studied and is believed to be related to chlorophyll and other pigments concentrations, leaf area index, and nutrient deficiencies (Curran et al., *Remote Sens. Env*. 35:69–76 (1991); Danson, F. M. et al., *Int. J. Remote Sens*. 16:183–188 (1995); Boyer et al., *Remote Sens, Env*. 25:71–87 (1988)).

Interpretation of the signal received from remote sensing is challenged by contributions to the spectra from atmospheric scattering, background soil reflectance, leaf angle distribution, and physical characteristics of the canopy, among other factors. Spectra might be governed by a small number of physical parameters jacquemond, S. et al., *Remote Sens. Env*. 34:75–91 (1990)). Because water stress may alter cellular structure and affect spectra, it is suggested that the visible to near infrared region may be more responsive than the infrared region to changes due to water stress (Cohen, W. B., *Intl. J. Remote Sens*. 12:1865–1876 (1991); Myneni, R. B., et al., *Remote Sens. Env*. 51:169–188 (1995)). There is a strong argument in the literature for the need to better understand leaf internal microscopic structures and their perturbations to the signal received from remote sensing. The microscopic embodiment of digital imaging spectroscopy as provided by HIRIM is ideally and uniquely suited for this need.

HIRIM will provide the capability to perform simultaneous analyses of the spectral and spatial information at a variety of magnifications using different microscope objectives. The spatial range can be extended even further, to cover the analyses of intact plants and whole leaves using KAIROS' software and digital imaging spectrophotometers to recall spectra from specific physiological features such as veins, petioles, sepals, stamens, and carpels. This is an advantage to single reflectance measurements obtained on cored leaf sections or dried and powdered plant material. As noted, it is difficult to extrapolate these such spectral relationships to estimates of protein, lignin and starch content of materials which have not undergone such treatment (Curran, P. J., *Remote Sens. Env.* 30:271–278 (1989)).

Similar to the work with algae described above, a DIS database of leaf thin sections that will be useful for establishing laboratory based microscopic assays for plant stress and its correlations to remote sensing data can be obtained. Senescence at the level of individual cells, entire organs or in some cases, the whole plant, could be followed using KAIROS' digital imaging spectrophotometers. The optical density of eukaryotic algal chloroplasts indicates that it should be possible to measure carotenoid and other pigment spectra from individual chloroplasts. It may also be possible to separately analyze the crimson, reds, and purples of anthocyanins and brown tannins located in vacuoles. Various leaf thin sections will be analyzed by HIRIM. The spectral and spatial distribution of pigments will be determined in healthy tissues and in tissues from plants that have been subjected to various environmental stresses.

Additional plant applications could include phototropism and photoperiodism. Positive phototropism is the bending of plant shoots towards light. This adaptive response is associated with a redistribution of chemical auxins which stimulate cell elongation on the side furthermost away from light. Although it is not known how light induces redistribution, it is believed that a yellow pigment related to riboflavin is the photoreceptor (Campbell, N. A., "Biology," 2nd ed., Benjamin Cummings, Redwood City, Calif. (1990)). Photoperiodism is the mechanism whereby different colors of light affect the periodic control of flowering, seed germination, and other plant functions. A photoperiod is detected by leaves. If only one leaf is left attached to a plant, a photoperiod is detected and floral buds induced. This signaling process is controlled by phytochrome which absorbs at 660 nm or 730 nm depending on the structural configuration of the chromophore.

Because plant tissues are already pigmented, it seems most appropriate to develop microscopic assays which preserve native spectra during sample preparation for HIRIM. The rapid freezing of samples in liquid nitrogen (to avoid solvents e.g., DMSO) can minimize destruction of tissue through microcrystalline ice formation during freezing, prior to sectioning on a microtome. The temperature of the block will be raised to approximately -20C for plant tissue and sections will be cut using a 'vibratome' microtome without embedding. Sections will be viewed at room temperature without fixation. Mild fixation will also be considered, but the rigidity of the plant tissue is expected to maintain the integrity of the section. Fixation with various cross-linking agents runs the risk of denaturing the tissue's spectrum.

Interactions attributable to pigment-protein are responsible for many of the spectral shifts observed in the light harvesting complexes of plants within the thylakoid membranes of the chloroplast. These interactions are easily disrupted by heat and solvents, but may be stable in milder imbedding procedures, such as paraffin. Many other fixation and embedding parameters are considered below for histological H&E staining.

Material Sciences: Mineral Thin Sections

The origin of electronic absorption spectra which are of interest in the planetary and mineral sciences are due to a variety of physical effects: 1) crystal field or ligand field transitions, 2) charge transfer transitions, and 3) electronic transitions which arise as a result of charge distribution in the crystal lattice. Detailed discussions of these types of electronic spectra can be found in advanced inorganic and physical chemistry treatises (see, Er-Rakho, L. et al., *J. Solid State Chem.* 37:151–156 (1981). Bednorz, J. G. et al., *Z. Phys. B—Condensed Matter* 64:189–193 (1986)). Much information can also be obtained from the vibrational spectra of minerals which give rise to transitions in the infrared.

An excellent account of various forms of spectroscopy as it is applied to remote geochemical analysis can be found in Pieters, C. M., and Englert, P. A. J., (eds) "Remote Geochemical Analysis: Elemental and Mineralogical Composition." The Cambridge University Press (1993). This collection of papers addresses topics on the planetary scale. This aspect of the invention adapts such an application to a microscopic level.

Ligand field or crystal field absorptions are caused by incompletely filled d orbitals of the transition metals. First series transition metals (Sc, Ti, V, Cr, Fe, Co, Ni, Cu) are often found in common rock-forming minerals and produce diagnostic absorptions such as for pyroxene, olivine, and numerous ferric oxides (Pieters, C. M., and Englert, P. A. J., (eds) "Remote Geochemical Analysis: Elemental and Mineralogical Composition." The Cambridge University Press (1993); Langer, K. et al., In, *Advanced Mineralogy: Instrumentations, Results, and Recent Developements*, A. S. Marfunin, ed., Springer-Verlag, New York; Amthauer, G. et al., *Physics and Chemistry of Minerals*. 11:37–51 (1984); Burns, R., "Mineralogical Applications of Crystal Field Theory", Cambridge University Press, (1970)). In addition to the cation itself, factors that affect crystal field spectra include the composition and geometry of near neighbors as well as symmetry distortions of the crystal lattice. The intensity, number of peaks, and spectral shape vary depending on the quantum mechanical selection rules and whether the cation is octahedrally or tetrahedrally coordinated. Crystal field spectra are therefore, useful indicators of physical effects, including: temperature, pressure, humidity, vitrification, and shock treatments. The intense blue color of sapphire is the most popular example of charge transfer transitions in mineralogy. This color is a result of a few hundredths of one percent of iron and titanium impurities substituting for aluminum in corundum ($Al_2O_3$) (Mattson, S. M. et al., *Physics and Chemistry of Minerals* 16:78–82 (1988); Nassau, K., "The Physics and Chemistry of Color," Wiley, N.Y., (1983)). When $Fe^{2+}$ and $Ti^{4+}$ ions are in adjacent octahedral sites and there is enough orbital overlap to interact, the following photochemical redox reaction can occur.

$$Fe^{2+}+Ti^{4+} \rightarrow Fe^{3+}+Ti^{3+} \qquad \text{Eq. 4}$$

This transfer of charge results in a broad absorption centered at 588 nm. In addition to metal-metal charge transfer, metal-oxygen, and other metal-ligand charge transfers are also known (Nassau, K., "The Physics and Chemistry of Color," Wiley, N.Y., (1983)). For example, the deep color of most mixed valence transition metal oxides such as manganite $Mn_3O_4$, magnetite ($Fe_3O_4$), and many other iron oxides can be attributed to charge transfer.

One of the determining factors for whether charge transfer or crystal field effects are responsible for a particular absorption band is to measure spectral properties with changes in pressure and temperature (Mattson, et al., et al. *Physics and Chemistry of Minerals* 14:94–99 (1987)). Since the probability of charge transfer transitions are a function of interatomic distances, raising the temperature will increase the bond length and decrease the intensity of the charge transfer peaks. On the other hand, crystal field transitions such as the thermochromism seen in ruby produce a shift in the position of peak maximum but no change in intensity.

A third mechanism of electronic transition is due to the formation of color centers. Color centers arise from displaced electrons trapped in a lattice defect. These electronic absorptions are quantum mechanically allowed and give rise to intense blue, yellow, green, and purple colors. Despite the intensity of these transitions, there are no absorption bands known to be attributable to color centers in the reflectance spectra of solar system objects. This is most likely because naturally formed, stable color centers occur infrequently and require very high energies on the order of tens of Kev—1Mev for formation. In Nature, this source comes from radioactive isotopes. Examples can be seen in the purple color of fluorite (often zoned) and colored halos surrounding radioactive inclusions in mica.

As might be imagined, the three color forming mechanisms described above can also serve as the basis for many additional ways to turn worthless stones into gems of extreme beauty. Unfortunately, it is sometimes impossible to tell the fake from its natural counterpart. However, in some cases such as turquoise and jade, it is possible to distinguish between the synthetic material and the real thing if a high resolution spectrum can be readily obtained.

Although HIRIM may be used as a quality control instrument in gemology, its has additional significant applications where it is not possible to obtain macroscopic samples. Laboratory experiments performed to mimic temperatures and pressures of the earth cannot be conducted on geologic timescales. It may be necessary to vary one factor at a time under these extreme conditions. As a result, the experimental products are generally microcrystalline or amorphous, showing exsolution, replacement, or phase separation on a microscopic scale Iron is the fourth most abundant element in the earth's crust and is found in many different minerals in various geometries. The crystal field spectra are sensitive to coordination changes as a result of differences in pressure and temperature. Crystal field stabilization energies may be a driving force for $Fe^{2+}$ partitioning in multiple phases such as that observed for iron, magnesium perovskites (Shen, G., et al., *Physics and Chemistry of Minerals* 20:478–482 (1994)). The Fe cation also plays an important role in physical properties such as electrical and thermal conduction. Iron spectral analyses are ideally suited to HIRIM measurements since they have a 85% probability of occurrence in the 50 to 1000 nm range. Spectra from multiple mineral grains under the microscope can be sorted and shifts due to changes in pressure and temperature easily displayed. The image processing capabilities of HIRIM can also be used to compile volume integration measurements of specific grains or phases based on feature extraction at selected wavelengths of interest.

One aspect of the present invention concerns a petrographic microscope. Petrographic microscopes are significantly different from microscopes used for biological samples. The objectives in a petrographic scope have larger working distances and may have an additional requirement that the lens glass be strain free. Mineralogists are used to making polarization measurements and analyzing interference figures as additional information for mineral identification and orientation. For this purpose, a petrographic microscope has a rotatable stage as well as Nicol prisms. Interference figures are created with the help of a Bertrand lens, a gypsum plate and/or a quartz wedge.

The ligand field spectra of transition metals have been used as temperature indicators in systems where physical access is difficult. For example, $Cu_2HgI_4$ is red at room temperature, black at 70C, red at 160C, and a deep red at 220C. Spatial information may be preserved without moving the sample and one may continuously monitor such changes spectroscopically using temperature controlled stages. Alternatively, HIRIM can also be used to study irreversible thermochromy wherein color indicates the highest temperature to which a substance was exposed.

Another application which may benefit from a temperature controlled stage is in the bleaching of color centers by exposure to heat. The thermoluminescence emitted as color centers are emptied, have been used to date rocks and minerals as well as pottery and other archeological artifacts (Nassau 1983). This process could conceivably be monitored by a change in peak intensity. Another application of HIRIM to the analyses of color centers might be as a radiation dosimeter. For example, HIRIM might be used to document the analyses of radiation induced color changes in the microstructure of cements in radioactive waste containers.

Medicine and Biotechnology: Biopsied Tissues

Many advances have occurred in microscopy since the invention of the brightfield optical microscope, including electron microscopy, fluorescence microscopy, and atomic force microscopy. Notwithstanding the power of these new techniques in the analysis of biological materials, the brightfield microscope remains the primary tool of pathologists in the initial survey of biopsied tissue.

Hematoxylin and eosin (H&E) stains are performed on almost all biopsied tissues before any other special stain or immunochemical analysis is considered, and may therefore be considered in exemplifying the use of the present invention in medicine and biotechnology. There are on the order of 10,000 H&E stained thin sections analyzed per day in the US. H&E's widespread use in histology (Prento, P. et al., In: *Theory and Strategy in Histochemistry*. ed: H. Lyon. Springer-Verlag, 107–119 (1991); Lillie, R. D., "H. J.s Conn's Biological Stains", 9th edition, Williams and Wilkins Co., Baltimore (1977); Clark, G., "Staining Procedures," 4th edition, Williams and Wilkins Co., Baltimore (1981)) has as much to do with the pathologist's familiarity and experience with this stain as it does with cost considerations. H&E is informative, inexpensive, and utilizes relatively low cost instrumentation (i.e., microtomes and brightfield microscopes). H&E stains cell nuclei, basophilic cytoplasmic structures, some elastic fibers and mucins a blue-purple, while most other structures are stained shades of red.

Despite its widespread and established use, there is no "standard H&E" stain. In fact, pure hematoxylin is white to yellowish in color (Green, F. J., "The Sigma-Aldrich Handbook of Stains, Dyes and Indicators", Aldrich Chemical Co., Milwaukee (1990)). In order to be used as a stain, hematoxylin is oxidized to hematein which then forms a colored metal complex. Procedures for this reversible oxidation reaction can be carried out by "ripening" or oxidation with exposure to air (for up to a period of 8 weeks, boiling the solution with HgO, addition of $NaIO_3$, or addition of ferric salts, peroxides or perchlorates (see, Clark, G., "Staining Procedures", 4th edition, Williams and Wilkins Co., Baltimore (1981)). In many cases, a further oxidized product, oxyhematein (brown) is irreversibly formed. Metal chelates of hematein range in color from red-violet to blue-black, depending on the metal. The result of stains using Al-hematein is strongly dependent on the molar ratio of Al:hematein, pH and ionic strength (Prento, P., and Schulte, E., In: *Theory and Strategy in Histochemistry*. ed: H. Lyon. Springer-Verlag, 107–119 (1991); Puchtler, H., et al., *Histochemistry* 85:353–364 (1986)). Al:hematein solutions are red at low pH and blue at high pH. This acid/base indicator property is used to advantage in H&E staining. However, the exact pH is difficult to control and will be a function of the redox potential as well as the stepwise association of $SO_4=$ (from the alum added), among other factors.

Eosin Y is the most commonly used counterstain for hematoxylin. According to *Staining Procedures Used by the Biological Stain Commission*, (Clark, G., "Staining Procedures", 4th edition, Williams and Wilkins Co., Baltimore (1981)) "the range in individual preferences for the intensity of the eosin stain is so great that only approximate staining and dehydration times can be suggested . . . procedures are tentative and must be adjusted to suit the individual preference." In fact, eosin B is often substituted for eosin Y to give a slightly pinker cytoplasmic stain lacking the yellowish tinge of eosin Y. Furthermore, phloxine is sometimes added for additional "red" colors.

There is some uncertainty as to the actual chemical formulae of hematoxylin derivatives (e.g., Alum-hematein) and the structure of possible protein or DNA adducts. Except for a spectrum of hematoxylin in methanol given in the *Sigma-Aldrich Handbook of Stains, Dyes and Indicators* (Green, F. J., "The Sigma-Aldrich Handbook of Stains, Dyes and Indicators," Aldrich Chemical Co., Milwaukee (1990)), no purification or spectral characterization of these putative hematein derivatives can be found. It is suspected that several different reactions occur between Al-hematein and biological substances and that this affects the spectrum of the chromophore.

The Biological Stain Commission (BSC) was established in the 1930's in response to a request from dye manufacturers and suppliers to set standards across the industry. Certification of dyes is required by the FDA. The methods for testing biological stains include both chemical and histological criteria as described in Chapter 20 of *Conn's Biological Stains* (Lillie, R. D., "H. J.'s Conn's Biological Stains," 9th edition, Williams and Wilkins Co., Baltimore (1977)). However, no absorption characteristics for hematoxylin are given.

The discussions above indicate that the staining process is difficult to control, and that the information obtained from a stained thin section is often based on very subtle color differences. Standardization and visual enhancement of such differences would benefit the entire histology community.

As can be seen in the above discussion, H&E stains have a rich chemistry and a broad range of colors which, despite its long and established use (since 1865), has not been well studied. In accordance with the methods of the present invention, HIRIM may be employed to accentuate the subtle color differences of cellular and subcellular features in H&E stained thin sections of biopsies by HIRIM analyses. Parameters that can be explored include: Type of tissue; Normal or abnormal tissue; Degree of autolysis of the tissue; Method of processing; Type of mounting medium, slides and coverslips (refractive index); Type of "Paraffin" used for infiltration; Thickness of tissue section cut on the microtome; Type of Hematoxylin (Mayers, Harris, or Gill); Type of Eosin (alcoholic, aqueous, or combined with phloxine); and Alternative methods using frozen sections.

Differentiation of tissue types will be based on shifts in the wavelength of maximal absorbance, an effect that is due to a variety of physicochemical parameters including ligand field and Forster mechanisms (Turro, N. J., "Modern Molecular Photochemistry," Benjamin Cummings (1978)). These in turn are based on distances and geometries among dye molecules which might form excitons leading to redshifts. Spectral shifts can also be expected if the dye molecules are attached at sites where point charges from amino acids or other biopolymers are in close proximity to the aromatic macrocycle of the dye molecule.

H&E stained sections of cardiac tissue for amyloid which is characteristic of certain types of cardiomyopathy (Roberts, W. C. et al., *Amer. J. Cardiol.*, 52:137 (1983); Olson, L. J., et al., *New Eng. J. Med.*, 317:738–742 (1987); Pepsys, M. B., *Quart. J. Med.*, 67:283–298 (1988)) reveal subtle differences in pink colors that would aid the pathologist in differentiating amyloid from normal connective tissue if these color differences could be accentuated. This is a case where morphological differences may be inadequate for differentiation and a colorimetric aid could be definitive. In this particular case, current technology would require a Congo Red stain to verify the presence of amyloid. The specialized stain would be delayed relative to the initial observation and could not be taken on exactly the same group of cells originally stained with H&E. Furthermore, an additional cost would be incurred. HIRIM's ability to detect amyloid in cardiac tissue would be a prelude to the analysis of other tissues wherein the presence of amyloid is indicative of disease.

Additional Applications

The HIRIM and methods of the present invention may be used for a variety of additional purposes, such as:

A. As evidenced from the intense coloration of multiple bands in Winogradsky columns, soil organisms can also be highly pigmented. Soil microbial populations could be used to assess environmental effects such as acid mine drainage, deforestation, pesticides, and fertilizers.

B. Phytoplankton blooms of toxic prymnesiophytes and dinoflagellates are responsible for the red tide which is devastating to both human health and the shellfish industry. HIRIM monitoring of microorganism populations could be used to predict and map these occurrences.

C. The ability to identify specific organisms could be correlated with regions producing higher commercial fishing yields. HIRIM could be used to monitor the microbial flora in aquaculture which result in high productivity.

D. Phytoplankton community structure might be used to assess environmental pollution factors (e.g., phytoplankton populations near the mouth of the Mississippi river and effects of application of herbicides in the Midwest). Distribution of marine organisms might be used to chart the progress of bioremediation efforts in the cleanup of oil spills.

E. Provided that spectroscopic measurements are in the visible and near IR, HIRIM could be used in the analysis of mineralogical thin sections. Vibrational spectroscopy in the IR would require a change in the currently proposed detector.

Having now generally described the invention, the same will be more readily understood through reference to the following examples which are provided by way of illustration, and are not intended to be limiting of the present invention, unless specified.

EXAMPLE 1

Instrument Development

Figure 2:
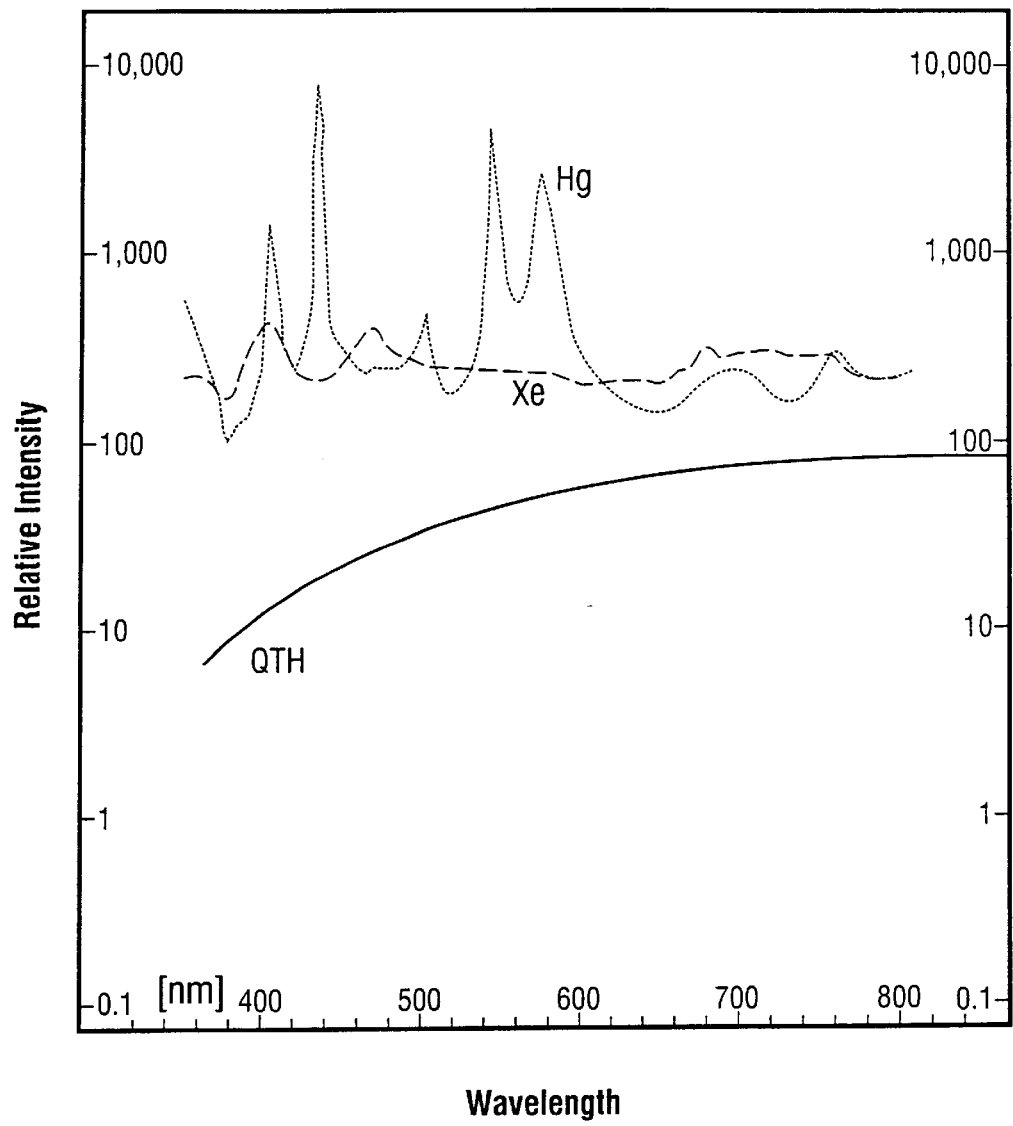
FIG. 2 shows relative spectral irradiance curves for quartz-tungsten-halogen (QTH), mercury, and xenon lamps. QTH has a logarithmic, monotonic drop-off in intensity in the blue, whereas multiple narrow band emissions are found in mercury and xenon lamps.

In order to obtain radiometrically calibrated spectra, one must correct for the spatial and wavelength responses of the light source, monochromator, relay optics, and detector. Relative spectral irradiance curves for quartz-tungsten-halogen (QTH), mercury, and xenon lamps are shown in FIG. 2. QTH has a logarithmic, monotonic drop-off in intensity in the blue, whereas multiple narrow band emissions are found in mercury and xenon lamps.

In constructing the HIRIM of the present invention, a newly developed CCD camera was incorporated into its design. This new camera (designated K7) and the earlier CCD (K6) used in the ColonyImager have significantly different properties, listed in Table 1. However, both the K6 and K7 are Peltier cooled, and digitize to 16 bits, yielding a dynamic range of 0–65535 units of grayvalue (GV).

TABLE 1

| Attribute | K6 | K7 |
| --- | --- | --- |
| spatial resolution (pixels) | 375 × 242 | 765 × 510 |
| pixel size (microns) | 23 × 27 | 9 × 9 |
| chip size (mm) | 8.6 × 6.5 | 6.9 × 4.6 |
| transfer interface | serial | parallel |
| transfer time (sec) | 55 | 8 |
| dark current (e–/sec) | 30 | 0.2 |

The major advantage of the K7 over the K6 is the increase in spatial resolution and decrease in the amount of time necessary to digitize and download an image. Whereas a spectral scan from 430 to 730 nm in 5 nm increments required a 1 hour run using the serial K6 transfer, the equivalent K7 scan can now be acquired in less than 10 minutes because the latter camera downloads data through the computer's parallel port. The K6 was employed as the HIRIM detector while camera drivers were developed for the K7. In addition, for better time management, this permitted differentiation between possible optical artifacts arising from the microscope as opposed to any artifacts that might be created by a new, untested detector.

A driver for communications between the PC and K7 camera was developed using low level C code that addresses the camera hardware directly. These functions were then incorporated into a Microsoft Windows program. Camera functions included: 1) establishment of communications protocols via the parallel port, 2) controls for temperature, 3) shutter control, 4) exposure time, and 5) data desampling and transfer options. The latter option enables the user to download an entire image versus a given region of interest (ROI).

Unexpected differences between the K6 and K7 were observed. For example, the K7 was found to have a large bias frame due to its method of digitization. This is effectively seen as an increase in the baseline counts. The two K7 detectors which have been investigated thus far have bias frames of approximately 2000 and 3000. The bias is constant for each camera and does not change with longer integration times; therefore, it can be easily subtracted. Although the bias is a relatively large number, the variations observed in grayscale within a dark frame are far better than gaussian or square-root-of-n statistics (ca. 10 GV). Other findings from these initial tests indicate that the K7 has extremely low noise, although a few hot pixels were detected.

Some CCD chips exhibit low frequency spatial distortions (the "zebra butt effect") which are wavelength dependent. The exact cause is unknown, but it is believed to be related to the narrow band nature of the incident light (filters that are used to simply acquire images from a microscope are usually cut-off or broad-band filters) interacting with thin films on the chip. This artifact affects spectra with very low absorbance, at ODs less than approximately 0.01. Although this effect was observed for the K6 on the ColonyImager, no zebra butt ripples were detected in any K7 chips.

At the time of this writing, the K7 camera has been successfully coupled to the trinocular port of an Olympus BX60 microscope. Initial investigations of K7 indicate that the spectral response, low light sensitivity, and magnification (inherent to this physically compact chip) are superior to the K6. Most importantly, the image digitization and download time is 25 times faster for binned images from the K7 as compared to the K6.

The attachment and optical alignment of the monochromator to the illumination optics of the scope was more complex than anticipated. It was determined that redirection of light using a plano concave substage mirror was not ideal, and that it was better to directly couple the output of the monochromator using a fiber optic. A fiber optic adapter was machined to fit into the illuminator port of the brightfield microscope. In order to optimize light throughput, the focal length of the first lens in the microscope's illumination system was matched to the fiber optic bundle output as if it were held at a position in space corresponding to the normal QTH lamp.

The most critical component which determines the resolution and magnification obtained with a microscope is the objective. The quality of an objective is measured by its ability to correct chromatic and spherical aberrations. Chromatic aberration is due to the inability of the objective to focus light of different wavelengths at the same point. Spherical aberration is due to the inability to bring to focus at the same point, the light that passes through the periphery of the lens and the light that passes through the center. An achromatic objective has been corrected at two wavelengths, red and blue for chromatic aberration and at a third wavelength in the yellow or green for spherical aberration. An apochromatic objective or apochromat is color corrected at three wavelengths (red, yellow, and blue) and spherically corrected for two wavelengths. Objectives that contain $CaF_2$ or the mineral fluorite, are also known as semi-apochromats. The quality of these objectives fall between an achromat and an apochromat.

As can be seen, the selection of a microscope and its objective lenses is not a trivial matter especially as the goal is to obtain radiometrically calibrated spectra from essentially every pixel in each image. One aspect of the present invention concerns the demonstration that the HIRIM can analyze samples that are on the order of a few microns and approach the limit of refraction for the visible region of the electromagnetic spectrum. Although differences in grayvalue which are attributable to refraction, diffraction or dispersion will contribute to optical artifacts in the data unless properly corrected, preliminary data from the HIRIM invention show that it is indeed feasible to obtain the ground state absorption spectra of single microbial cells.

EXAMPLE 2

Analysis of Marine Phytoplankton

The BoothBay Harbor strain collection is the world's largest collection of marine phytoplankton and includes over 1500 different organisms. A pilot study of approximately 25 different species represents a diverse spectral 'palette' that may be extended to other members of this collection or to other collections and isolates. It is expected that Brownian motion and/or organism motility will require that organisms be immobilized on standard glass microscope slides. This will be performed using polylysine or by air drying under conditions that do not disrupt the microorganisms or their pigment-protein complexes. Since polylysine is a clear substance, it should not interfere with spectra in the visible or near IR. Spectra will be taken of hundreds of individual organisms from pure culture to establish the range in spectra variability normally present in the population. Diverse populations on a single slide will be created by mixing aliquots of pure culture. Composite spectra of several organisms will be taken by combining multiple cells into a single feature. This could then be used as a test for spectral deconvolution algorithms such as Principle Components Analysis and other multivariate methods (Yang, M. M., "Raman Spectroscopic Investigations of Hydrothermal Solutions", Doctoral Thesis, Princeton University, 1987).

In addition to samples supplied by scientists in the field, pure cultures of freshwater and marine organisms were obtained from the Center for Culture of Marine Phytoplankton (CCMP). Organism selection was based on a variety of factors, including pigment composition: *Prorocentrum lima* is a toxic dinoflagellate known to be involved in red tide blooms which are so devastating to the fish and shellfish industries (Moestrup, O., In, "The Haptophyte Algae,"J. C. Green et al. eds., Clarendon Press, Oxford (1994)). Tetraselmis sp., *Rhodomonas salina, Skeletonema costatum* are natural and abundant food sources in coastal regions. These marine algae are also widely used as fish feed in aquaculture. *Duniella tertiolecta* is a halophilic green algae farmed in many countries for beta-carotene production. The coccolithophore *Emiliania huxleyi* is a common open ocean, bloom-forming alga which has been associated with bright areas in airborne (AVHRR) and satellite (CZCS) images (Holligan, P., et al. *Nature* 304:339–342 (1983); Ackleson, G., *EOS* 71:108 (1990)). These organisms play an important role in the global carbon cycle since their skeletal composition is almost pure calcium carbonate. In order to investigate the optical and spectroscopic properties of coccolith formation, two strains of *Emiliania huxleyi* were obtained, one with and one without coccolith formation. Table 2 lists the genus and species, class, average size, and major pigments of some of the eucaryotic algae studied (only CCMP strains are listed). In Table 2, CCMP is the strain collection number assigned by the Center for Culture of Marine Phytoplankton. Species which did not survive shipment are not listed. The following pigment abbreviations apply: chl chlorophyll, AP allophycocyanin, PE phycoerythrin, PC phycocyanin, car carotene, fux fucoxanthin, lut lutein, vio violaxanthin, and zea zeaxanthin.

TABLE 2

| Class | CCMP no. | Genus and Species | Size/$\mu$m | Major Pigments |
|---|---|---|---|---|
| Chlorophyceae | 232 | Chlamydomonas sp. | 3–6 × 3–7 | chl a, b, car, lut, vio, zea |
|  | 258 | Chlorococcum sp. | 4–12 |  |
|  | 259 | *Chlorosarcinopsis halophilia* | 12 |  |
|  | 1320 | *Dunaliella tertiolecta* | 6–9 |  |
| Prasinophyceae | 903 | Tetraselmis sp. | 15–20 × 10–15 | chl a, b, c lut, zea |
|  | 1203 | *Pycnococcus provasoli* | 3 |  |
| Xanthophyceae | 1275 | *Tribonema aequale* | (filamentous) | chl a, c |
| Cryptophyceae | 1168 | *Chroomonas mesostigmatica* | 3–7 | chl a, c, AP, PC, PE, car |
|  | 1319 | *Rhodomonas salina* | 5–13 × 6–8 |  |
| Rhodophyceae | 1328 | *Porphoridium cruentum* | 5–8 | chl a, d, AP, PC, PE, car, lut |
|  | 1530 | Rhodosorus sp. | 5–8 |  |
| Prymnesiophyceae | 282 | *Chrysochromulina ericina* | 5–8 | chl a, c, car, fux |
|  | 284 | *Chrysochromulina herdensis* | 5–8 |  |
|  | 373 | *Emiliania huxleyi* | 4–8 |  |
|  | 378 | *Emiliani a huxleyi* | 4–8 |  |
| Chrysophyceae | 678 | Poterioochromonas sp. | 4–7 | chl a, c, car, fux, vio |
| Dinophyceae | 685 | *Prorcentrum lima* | 45–48 × 30–33 | chl a, b, c, fux |
| Coscinodiscophyceae | 1315 | *Chaetoceros calcitrans* | 3–7 | chl a, b, c, car, fux, vio |
|  | 1332 | *Skeletonema costatum* | 6–8 | chl a, c, car, fux |
| Bacillariophyceae | 1405 | Amphora sp. | 3–4 × 7–9 | chl a, c, car, fux |
| Raphidophyceae | 1596 | *Heterosigma carterae* | 9–12 | chl a, c, car, fux, vio |

The diversity of the strain collection and the different habitats in which they are found, gives rise to a variety of media, temperature and other growth conditions. Some of the algae samples are very sensitive to environmental conditions and a few of the cultures did not survive shipment from the CCMP. Photosynthetic algae, like many land plants, may exhibit sensitivity to a photoperiodic cycle of day and night. One of the first tasks was to construct a temperature controlled environment with periodic illumination. A number of different media were also investigated so as to maintain the healthiest cultures possible. Some organisms thrive in thick dense cultures while others prefer less crowded conditions. These differences made it necessary to develop slightly different sample preparation procedures to obtain large numbers of spectra simultaneously.

In addition to the physical size of a cell, the number of cells in the field of view of the microscope at a given magnification are the limiting factors determining the simultaneous measurements that can be made on individual features during one spectral run. Using a vortexer and centrifuge, the sample may be concentrated. Because care must be taken so that cells are not disrupted and filaments unduly severed, this process is somewhat different depending on whether the organism is unicellular or filamentous. In some samples, (e.g., *Fremyella diplosiphon, Amoebobacter purpureus*) individual organisms form filamentous masses or flocculants which must be disassociated to obtain meaningful spectra. In these cases, gentle sonication and addition of detergents may be employed to separate these organisms.

As indicated above, Brownian motion and/or organism motility required that the algae be immobilized on glass slides. Many of the algae did not survive air drying and some cannot withstand heat. Therefore, it is advisable to embed the algae in an immobilizing matrix which does not contribute or adversely affect the optical or spectroscopic properties of the sample. Spectra were obtained in 2% low-melt agarose with 2% NaCl added for saltwater samples. The dissolved salt prevents the marine and/or halophilic organisms from lysing or bursting due to differences in osmotic pressure.

In general, cells were harvested in late exponential phase and concentrated by centrifugation in 1.5 ml aliquots at 8000 rpm for 1 minute in an Eppendorf tube. The supernatant was removed, and the pellet was dispersed and resuspended in new media by gentle pipetting. The sample was then vortexed for 5 seconds and the supernatant removed to leave an algal sludge. In addition to achieving higher algal concentrations, these conditions served to rid the sample of fine detritus and particulates which may interfere with spectra acquisition at a later time. Depending on the sample, a 2% agarose with or without NaCl was prepared. While still liquid, a drop of the agarose mixture and a drop of the cell suspension was mixed on a microscope slide and a coverslip immediately pressed down. Vaseline was then applied to the edges of the coverslip to prevent desiccation. In certain instances, this method of sample preparation has provided reproducible spectra for up to 24 hours. Slides with a single culture, as well as slides with a combination of several different species, were analyzed.

Figure 3:
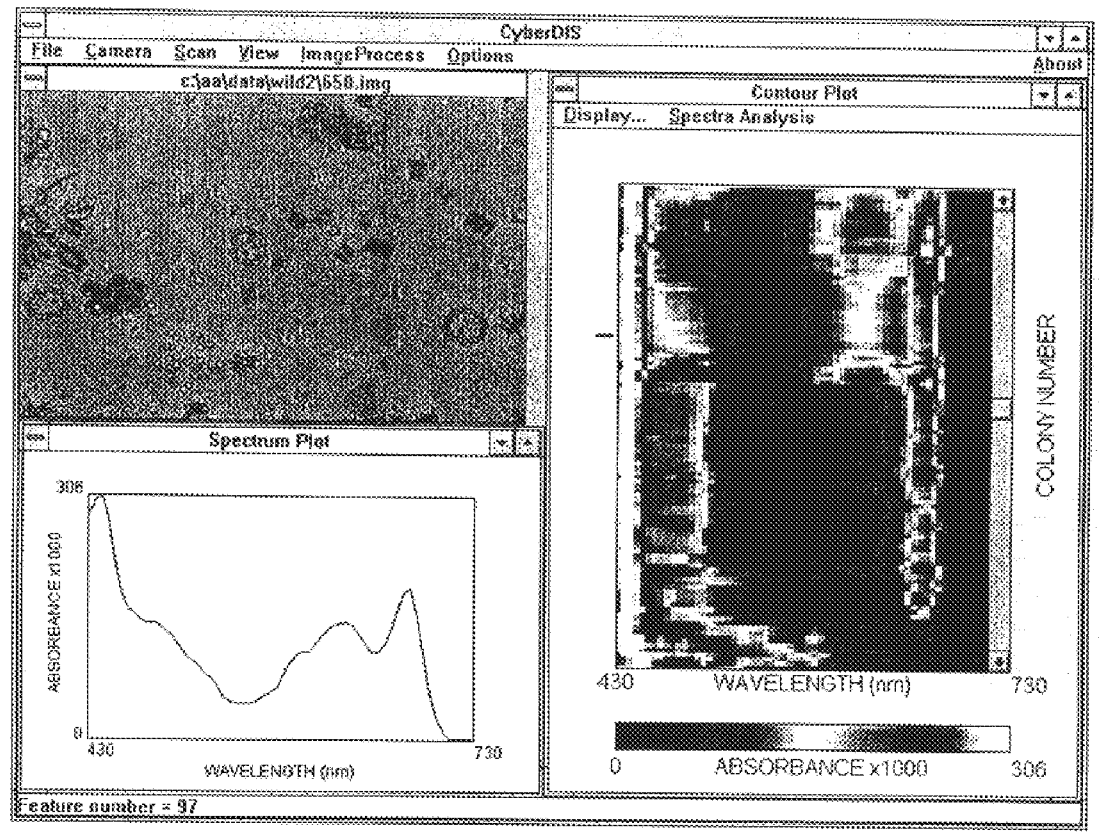
FIG. 3 is an image of the CyberDIS user interface showing data acquired from a field sample collected during a green algal bloom.

The use of the HIRIM of the present invention is illustrated in FIG. 3. The actual data contained in FIG. 3 utilized a field sample from the surface waters of Stow Lake, Calif.; during a green algal bloom. Under a 40× objective, this image shows a variety of cell types, including: chlorophytes, diatoms, and cyanobacteria. The current feature of interest is marked by a small white circle located in the lower left corner of the image. The spectrum of this organism is displayed in the lower left window as a conventional spectrum plot. One hundred and thirty individual spectra from 430–730 nm at 5 nm increments were simultaneously acquired in this dataset. As indicated by the presence of the scrollbar, only a fraction of these spectra are displayed in the contour plot.

As indicated, one of the unique features of the software interface for HIRIM is the ability to sort spectra and display them in the form of pseudocolored contour maps. The versatility and power of these functions are demonstrated using cultures of Rhodosorus, Chroosmonas, and Chlorococcum which were mixed and immobilized on a slide. Identification of these three algal types can easily be confused since all three are coccoid in shape and overlap in size over the range of 4–12 microns. The field of view for which the data in FIG. 4 were acquired, contained many intact cells as well as debris from the media and from cells which had lysed. No discrimination was given to features which were selected (i.e., both debris and intact cells were scanned). All 75 feature spectra are shown in each of the four panels in FIG. 4.

Figure 4:
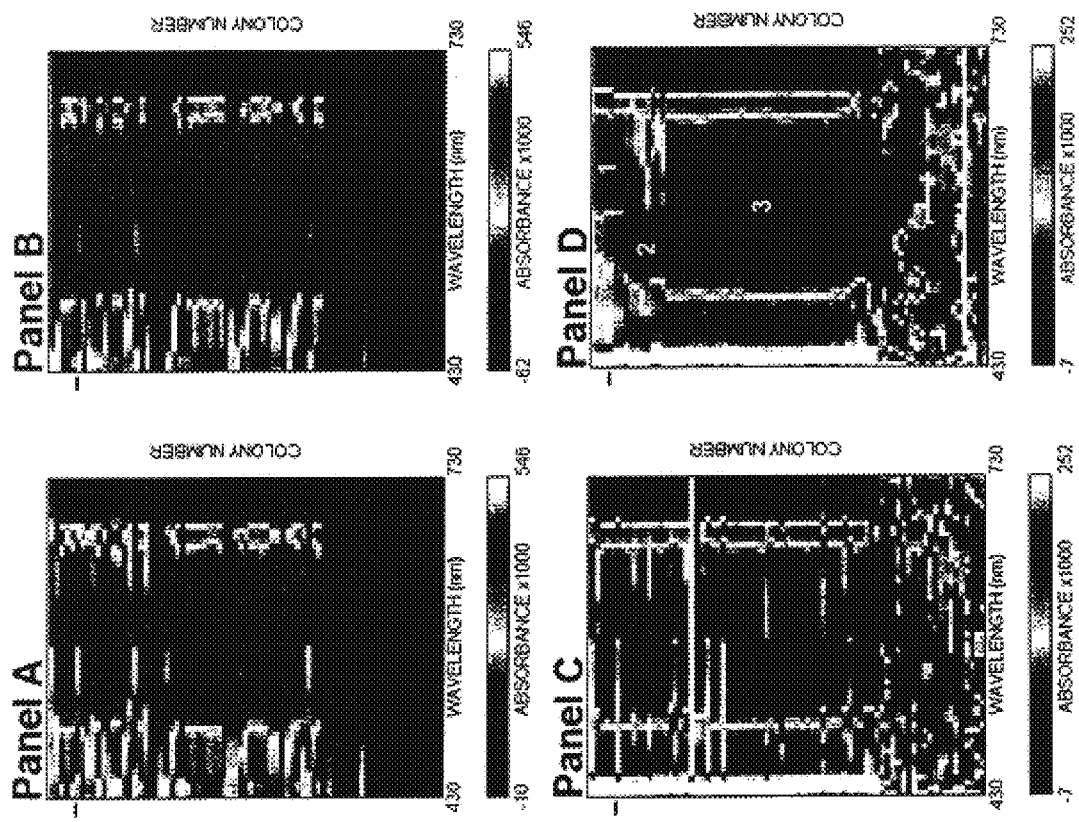
FIG. 4 shows the ability of the High Resolution Imaging Microscope (HIRIM) to sort spectra and display them in the form of pseudocolored contour maps. Seventy-five spectral features from a sample containing three different algal types are shown.

In FIG. 4, the unprocessed contour map as it is displayed immediately after the scan is shown in Panel A. In Panel B, a constant value was subtracted to the baseline in each individual spectrum so that the absorbance at 730 nm is zero. On the PC monitor, this adjustment is reflected as a thin vertical black stripe at the far right side of the contour plot. Due to the difficulties inherent in color hardcopy reproduction, only a few non-continuous shades of a given color are generated and so this change is seen as a solid dark blue, thick vertical section on the right. Despite this limitation, one can still readily identify peaks due to chlorophyll and other pigment spectra from the color printouts. Panel C shows the results of stretching each spectrum (i.e., row) to its individual minimum and maximum absorbances, whereas the pseudocoloring scheme in Panel A had encoded the highest and lowest values of the entire dataset. In Panel D, a least squares algorithm has been applied so that similarly shaped spectra are grouped together. As shown, there are three groups indicative of the three species which are present. In the same sorting process, all aberrant spectra arising from debris and other unidentifiable objects have been automatically grouped towards the bottom of the contour map. In addition to similarity, spectra can currently be sorted based on maximum absorbance, wavelength of maximum absorbance, and maximum absorbance at a particular wavelength. This development should be very useful in analyzing subtle spectral features such as the so called 'red-edge' as referred to in canopy and vegetation remote sensing.

Figure 5:
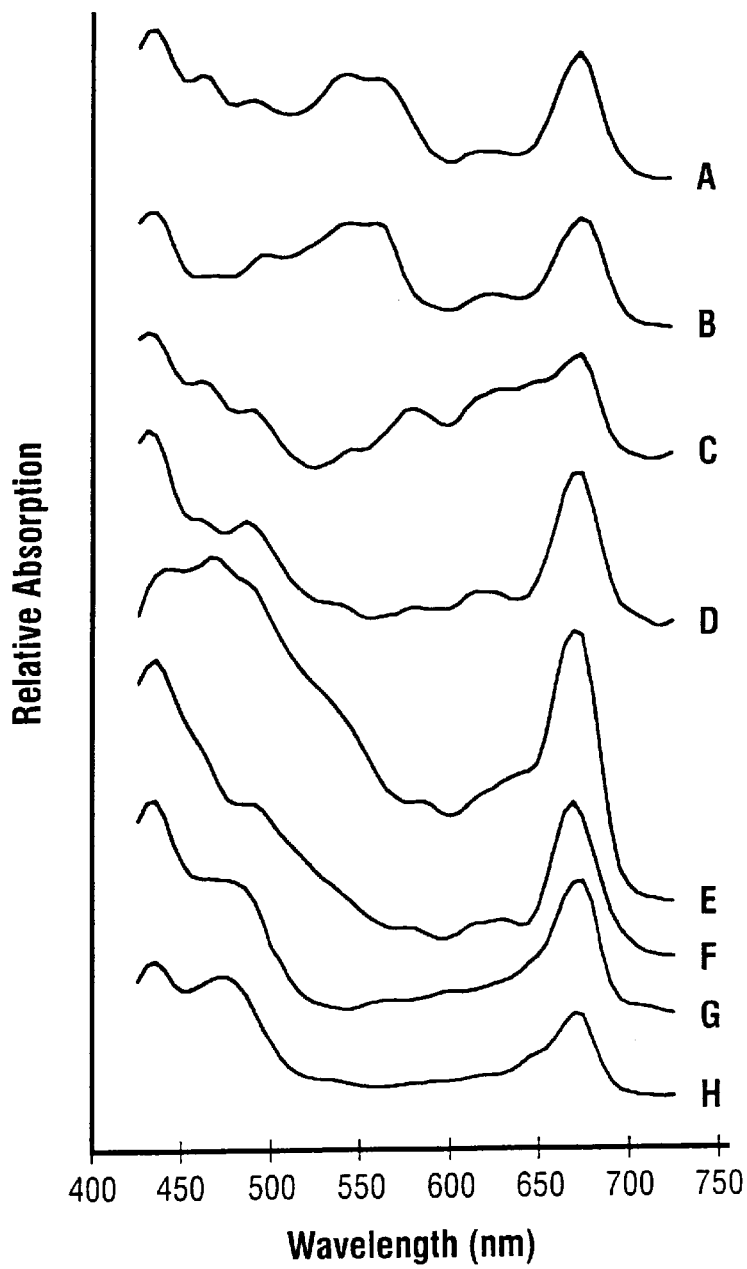
FIG. 5 shows typical single cell spectra of: A) *Rhodomonas salina*, B) *Porphyridium cruentum*, C) *Chroosmonas mesostigmatica*, D) *Tribonema aequale*, E) *Prorocentrum lima*, F) *Amphora* sp., G) *Dunaliella tertiolecta*, and H) *Tetraselmis* sp.

The organisms analyzed in the FIG. 4 are from the classes of Chlorophyceae, Cryptophyceae and Rhodophyceae. In FIG. 5, conventional spectral plots of eight different species representing 7 different classes are shown. These species are: A) *Rhodomonas salina*, B) *Porphyridium cruentum*, C) *Chroosmonas mesostigmatica*, D) *Tribonema aequale*, E) *Prorocentrum lima*, F) *Amphora* sp., G) *Dunaliella tertiolecta*, and H) *Tetraselmis* sp.

The chlorophyll a peak at 675 nm is apparent in all 8 spectra. A peak at 630 nm can be readily detected in the spectra of Rhodomonas, Tribonema, and Amphora and is attributed to the presence of chlorophyll c. Chlorophyll b is found in Tetraselmis, Dunaliella, and Prorocentrum. Its spectrum gives rise to a strong absorption at 480 nm and a weaker absorption peak at 650 nm. The latter is often seen as an asymmetric contribution to the stronger chlorophyll a peak at 675 nm. Phycobiliproteins are found in the Cryptophyceae and Rhodophyceae classes and are predominantly responsible for absorptions between 450–650 nm. Carotene and xanthophyll pigments generally absorb at higher energies and exhibit large spectral overlap in this region.

All of the spectra shown in FIG. 5 obtained by HIRIM correlate well with published spectra of extracted pigments or cell cultures taken on a conventional spectrophotometer with a scattering attachment (Hader, D. et al., "General Photobiology," Pergamon Press (1987); Rowen, K. S., "Photosynthetic Pigments of Algae". Cambridge Univ. Press, New York (1989)). These organisms vary significantly in size and required HIRIM to be used over a full range of magnifications: 10×, 20×, 40× air-based semi-apochromat, and the 100× oil immersion apochromat objectives. HIRIM was able to resolve spectral peaks in single cells of Fremyella which were not apparent using conventional spectroscopy on liquid cultures. This suggests that there are cell-to-cell variations that are averaged out by conventional spectroscopy (which determines the average spectrum of millions of cells).

Figure 6:
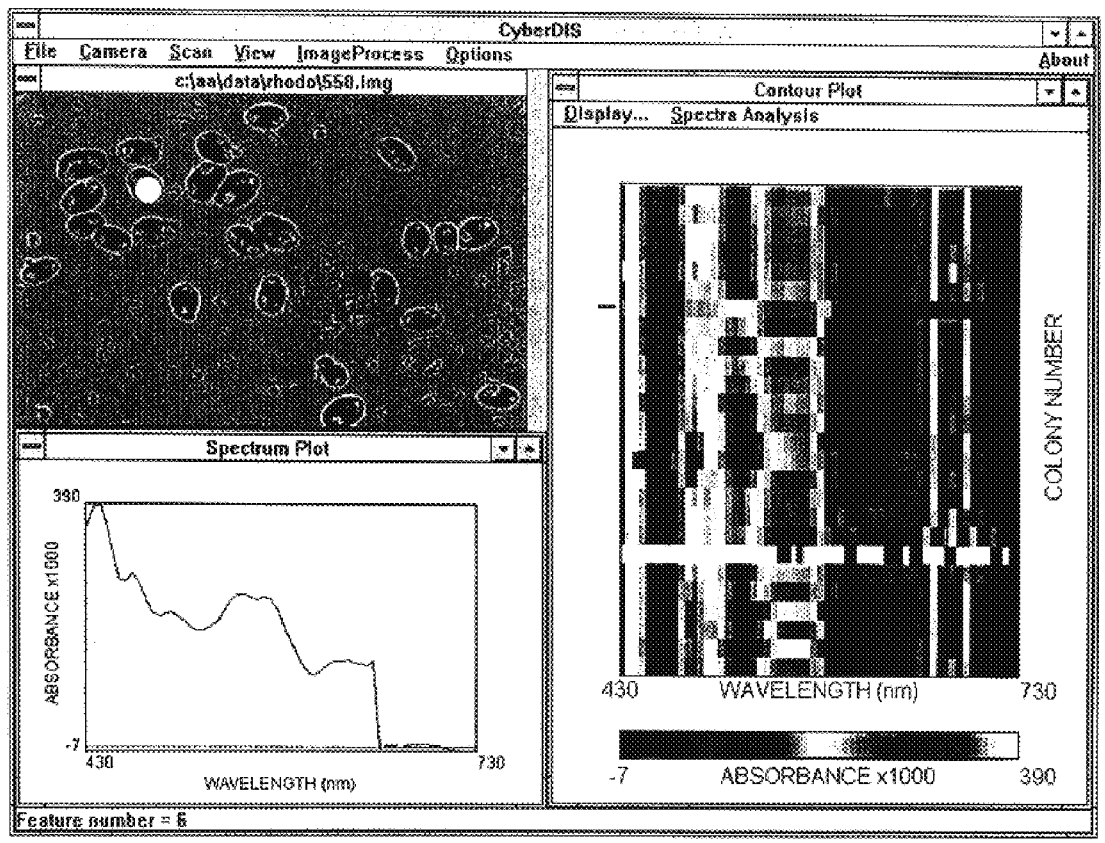
FIG. 6 provides a CyberDIS display of a *Rhodomonas salina* sample.

FIG. 6 shows aCyberDIS display of a *Rhodomonas salina* sample. Movement of the cell under selection is evidenced in later image comparisons (not shown in the Figure) and the sudden drop in absorbance after 650 nm.

During some HIRIM runs, spectra were observed which suggested feature movement. This is obviously more of a problem for 'live' samples embedded in agar than permanent thin sections. FIG. 6 shows data collected after a 1 hour scan of a sample of *Rhodomonas salina*. The 550 nm image is displayed. The highlighted feature rests on a cell whose spectrum is plotted. As can be seen, there is a sudden drop in intensity after 650 nm. This effect can be attributed to sudden cell movement that occurred during the scan, since an image taken at the end of the scan no longer shows this cell at the same location. This is an example where there has been radical movement. Additionally, some of the organisms studied may be undergoing small, localized motions or gyrations which are contributing to aberrant spectra, resembling noise. In both cases involving putative motion artifacts, it would be useful to store all images acquired during the scan which could then be displayed sequentially in order to visualize movement. This procedure would also be useful in detecting any changes in focus or other malfunctions that occur over time. Furthermore, the ability to run a HIRIM 'movie' would be useful to researchers studying samples in which movement is not an artifact, i.e., motility research.

CyberDIS is currently written with the assumption that all features of interest are known and selected before the scan. In cases where this is not true, spectra of unselected features cannot be determined after the run. Thus, it would be beneficial to be able to extract spectra from a pixel or group of pixels from a previously stored stack of images. Software enabling such a feature would enable researchers working with other types of spectrally 'stacked' images to take advantage of CyberDIS capabilities, including spectral sorting algorithms and contour map displays. AVIRIS data might be a good candidate database for such analyses.

For historical purposes, it is interesting to note that the early versions of CyberDIS were conceived to fulfill the need to rapidly screen large libraries of bacterial mutants from the surface of petri plates (Yang, M. M., 1994, Digital Imaging Spectroscopy of Microbial Colonies. *American Biotechnology Laboratory* May:18–20 (1994); Youvan, D. C., *Nature* 369:79–80 (1994); Yang, M. M. and Youvan, D. C. *Bio/Technology* 6:939–942 (1988)). This work was developed independently of the remote sensing community and was based on UNIX workstations. CyberDIS is written in C under MS Windows.

The implementation of DIS on a PC has effectively decreased the cost of imaging spectrophotometers by almost two orders of magnitude from some of the earlier systems. Coincidentally, the PC's compute power is now approaching the capabilities of early workstations.

In order to make CyberDIS' spectral sorting algorithms and display methods still more powerful, a pseudocolored contour plot of the spectral first derivative was implemented.

EXAMPLE 3

Analysis of Minerals

Figure 7:
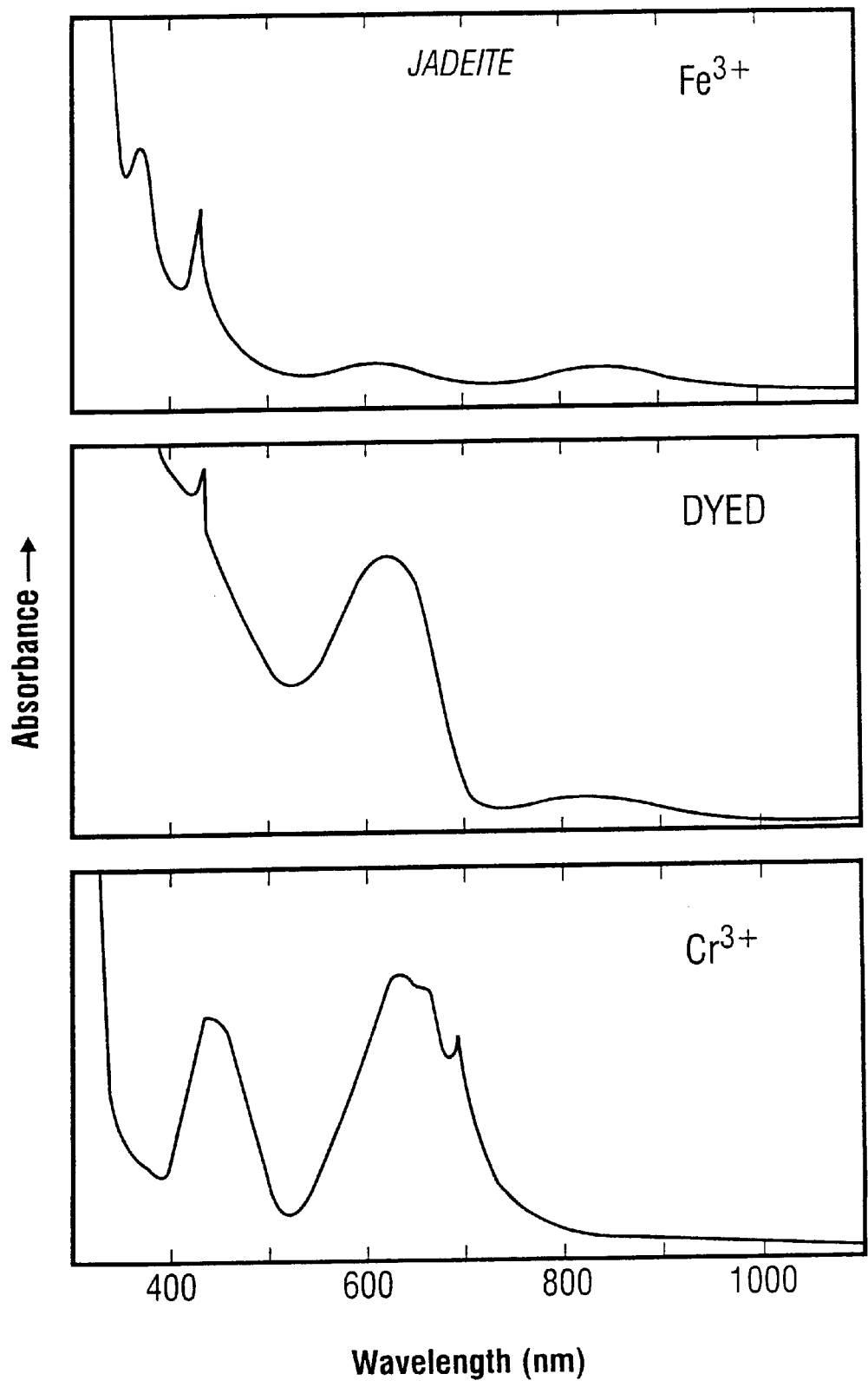
FIG. 7 shows the use of the present invention to evaluate minerals.

The use of HIRIM to evaluate minerals is illustrated in FIG. 7, which shows the spectral differences between naturally occurring jadeite whose color is due to trace amounts of Fe or Cr and that of an organically dyed, synthetic sample. Many of the spectral features and fine structures shown here would have been impossible to distinguish by eye.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for acquiring, sorting and displaying spectral information from a plurality of microscopic objects, including:

(a) acquiring at least one spectrum for each microscopic object within a field of view of a digital imaging detector, and (b) sorting the acquired spectra by a selected criterion; and (c) displaying the sorted spectra.

2. The method of claim 1, wherein chromophores in the microscopic objects generate the spectral information.

3. The method of claim 1, further including illuminating the microscopic objects.

4. The method of claim 1, wherein at least one of the microscopic objects emits fluorescence.

5. The method of claim 4, further including acquiring fluorescence emission images of the microscopic objects using a selected long-pass filter.

6. The method of claim 1, wherein at least one of the microscopic objects undergoes electronic transitions which arise as a result of charge distribution in a crystal lattice.

7. The method of claim 1, wherein the plurality of microscopic objects comprises at least one biological cell.

8. The method of claim 7, further including immobilizing the biological cells by attachment to a solid surface.

9. The method of claim 7, further including immobilizing the biological cells in a polymer matrix.

10. The method of claim 7, wherein the biological cells are permitted to move freely within the field of view of the digital detector.

11. The method of claim 1, further including using the spectral information to identify microorganisms based on spectral signatures.

12. The method of claim 11, wherein the microorganisms that are identified cannot be cultured.

13. The method of claim 7, wherein the biological cells comprise cells labeled with dye.

14. The method of claim 13, wherein the cells are labeled with hematoxylin and eosin.

15. The method of claim 1, wherein the microscopic objects consist of biological materials.

16. The method of claim 1, wherein the microscopic objects consist of components of biological cells.

17. The method of claim 1, wherein the microscopic objects are composed of non-biological material.

18. The method of claim 17, further including using the spectral information to identify defects or alterations in the material.

19. The method of claim 2, further including using the spectra of the chromophores to indicate the acid-base properties of the microscopic objects.

20. The method of claim 1, further including using the spectral information to indicate physical characteristics of the microscopic objects, including temperature, pressure, humidity, vitrification, and shock treatment.

21. The method of claim 1, further including using the spectral information to visualize protein or DNA adducts.

22. The method of claim 1, further including using the spectral information to standardize and enhance histological staining procedures for the microscopic objects.

23. The method of claim 1, further including applying dye molecules to the microscopic objects and using the spectral information to measure distances and geometries among the dye molecules in a sample of microscopic objects.

24. The method of claim 1, further including applying dye molecules to the microscopic objects and using spectral information in the form of spectral shifts to sense changes in the environment of the dye molecules in the microscopic objects.

25. The method of claim 1, further including using the spectral information to create datasets comprising stacks of spatially registered images taken at multiple wavelengths.

26. The method of claim 25, further including displaying images from the image stack as a movie sequence.

27. The method of claim 26, wherein displaying images from the image stack indicates spectral changes in the microscopic objects over time.

28. The method of claim 1, wherein sorting uses spectral deconvolution algorithms.

29. The method of claim 1, further including:
    (a) sorting and displaying the spectral information in a pseudocolored mode;
    (b) concurrently, sorting spatial information for the microscopic objects; and
    (c) displaying the spectral information and the spatial information in multiple windows of a graphical user interface such that there is real-time correlation for such information.

30. The method of claim 1, further including displaying the spectral information as a pseudocolored contour plot.

31. The method of claim 30, wherein displaying the spectral information as a contour plot uses a color scale to indicate the intensity or absorbance value at each point in a spectrum.

32. The method of claim 30, wherein the pseudocolored contour plot automatically groups aberrant spectra arising from unidentifiable objects.

33. The method of claim 29, further including providing a linkage between a window including a display of the spectral information, a window including a display of the spatial information, and a window including a display of an image of the microscopic objects, such that selection of a displayed picture element in any window results in a real-time update of corresponding displayed picture elements in the other windows.

34. The method of claim 33, further including a tool that enables a user to select one or more picture elements in an image and recall an associated spectrum.

35. A method for acquiring and displaying spectral information for each pixel of a digital image, including:
    (a) acquiring a plurality of digital images taken at multiple wavelengths, each digital image comprising a plurality of pixels each encompassing a microscopic region less than about 2 microns in size;
    (b) combining the digital images in stacks of spatially registered digital images;
    (c) determining a spectrum for each set of spatially registered pixels in the stacks;
    (d) sorting the determined spectra by a selected criterion; and
    (e) displaying the sorted spectra.

* * * * *